US006928326B1

(12) United States Patent
Levine

(10) Patent No.: US 6,928,326 B1
(45) Date of Patent: Aug. 9, 2005

(54) DIAGNOSIS OF FUSION OR PSEUDOFUSION

(75) Inventor: Paul A. Levine, Santa Clarita, CA (US)

(73) Assignee: Pacesetter, Inc., Sylmar, CA (US)

(*) Notice: Subject to any disclaimer, the term of this patent is extended or adjusted under 35 U.S.C. 154(b) by 227 days.

(21) Appl. No.: 10/405,212

(22) Filed: Mar. 31, 2003

(51) Int. Cl.$^7$ .............................................. A61N 1/05
(52) U.S. Cl. ..................................................... 607/122
(58) Field of Search ............................... 607/14, 15, 28, 607/122

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 4,944,298 A | 7/1990 | Sholder | 128/419 PG |
| 5,184,615 A * | 2/1993 | Nappholz et al. | 607/14 |
| 5,350,410 A | 9/1994 | Kleks et al. | 607/28 |
| 5,466,254 A | 11/1995 | Helland | 607/123 |
| 5,476,483 A | 12/1995 | Bornzin et al. | 607/17 |
| 5,713,934 A | 2/1998 | Leckrone | 607/28 |
| 6,314,323 B1 | 11/2001 | Ekwall | 607/23 |
| 6,324,427 B1 | 11/2001 | Florio | 607/28 |
| 6,434,428 B1 * | 8/2002 | Sloman et al. | 607/28 |

OTHER PUBLICATIONS

David Mendelowitz, "*Advances in Parasympathetic Control of Heart Rate and Cardiac Function*," News Physiol. Sci. (Aug. 1999) vol. 14, pp 155-161.

* cited by examiner

*Primary Examiner*—George Manuel

(57) ABSTRACT

Exemplary methods and devices for determining whether fusion or pseudofusion have occurred. An exemplary method includes delivering a stimulus, sensing cardiac activity, determining whether the stimulus resulted in capture, and if the determining indicates that the stimulus did not result in capture, then, determining whether the sensed cardiac activity includes characteristics of native cardiac activity by comparing at least some of the sensed cardiac activity to a template. Accordingly, if the sensed activity includes native activity, then a diagnosis is made that the stimulus resulted in fusion or pseudofusion. Another exemplary method includes determining whether a stimulus resulted in capture, and if the determining indicates that the stimulus did not result in capture, then, adjusting sensitivity of a sensor and sensing cardiac activity using the sensor. According to this method, if cardiac activity is sensed, then a diagnosis is made that the stimulus resulted in fusion or pseudofusion. Various methods and/or devices are suitable for use with autocapture. Other methods, devices and/or systems are also disclosed.

18 Claims, 12 Drawing Sheets

EXEMPLARY CARDIAC RHYTHM

EXEMPLARY WAVEFORMS

DIAGNOSIS OF FUSION OR PSEUDOFUSION

CROSS-REFERENCE TO RELATED APPLICATIONS

This application is related to copending U.S. patent application Ser. No. 10/405,210, titled "Diagnosis of Atrial Fusion, Atrial Pseudofusion and/or Native Atrial Activity," filed concurrently herewith.

TECHNICAL FIELD

Exemplary methods and/or devices presented herein generally relate to cardiac pacing and/or stimulation therapy. Various exemplary methods and/or devices concern recognition or diagnosis of fusion and/or pseudofusion.

BACKGROUND

Fusion is typically characterized by a wave complex formed by depolarization of the myocardium initiated by two different foci, commonly a non-native stimulus as from a pacemaker or ICD and a native stimulus. Pseudofusion is typically characterized by a wave complex formed by depolarization of the myocardium initiated by a native stimulus; however, a non-native stimulus, that does not contribute to depolarization, is present and distorts the wave complex.

Various fusion and/or pseudofusion scenarios may cause a pacing device to waste power and to deliver non-optimal or inadequate therapy. In particular, fusion and/or pseudofusion may cause a pacing device to deliver a stimulus where native activity would suffice. In addition, in a pacing scheme that implements a ventricular autocapture algorithm to set a ventricular stimulus power level, fusion, and/or pseudofusion may cause the algorithm to set too high of a ventricular stimulus power level. To minimize the risk of setting an inappropriate power level, various ventricular autocapture algorithms rely on some degree of fusion and/or pseudofusion avoidance algorithms. For example, if non-capture is diagnosed following a primary stimulus pulse, then a back-up pulse is delivered and, on the next cycle, the AV delay (or PV delay) is extended (e.g., by approximately 100 ms). An inference is then made that the diagnosed loss of capture is due to fusion if a native R wave is detected within this extended AV delay.

While autocapture algorithms that account for fusion and/or pseudofusion exist, they are generally limited. Thus, a need exists for recognition algorithms that can more accurately recognize fusion and/or pseudofusion. Various exemplary methods and/or devices are described below which may address this need and/or other needs.

SUMMARY

Exemplary methods and devices for determining whether fusion or pseudofusion have occurred. An exemplary method includes delivering a stimulus, sensing cardiac activity, determining whether the stimulus resulted in capture, and if the determining indicates that the stimulus did not result in capture, then determining whether the sensed cardiac activity includes characteristics of native cardiac activity by comparing at least some of the sensed cardiac activity to a template. Accordingly, if the sensed activity includes native activity, then a diagnosis is made that the stimulus coincided with a native depolarization resulting in fusion or pseudofusion. Another exemplary method includes determining whether a stimulus resulted in capture, and if the determining indicates that the stimulus did not result in capture, then adjusting sensitivity of a sensor and sensing cardiac activity using the sensor. According to this method, if cardiac activity is sensed, then a diagnosis is made that the stimulus coincided with a native depolarization resulting in fusion or pseudofusion.

Various exemplary devices for performing such exemplary methods are also disclosed herein along with a variety of other exemplary methods and/or devices. In general, the various devices and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations.

This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate nerves and/or stimulate and/or shock a patient's heart.

Figure 1:
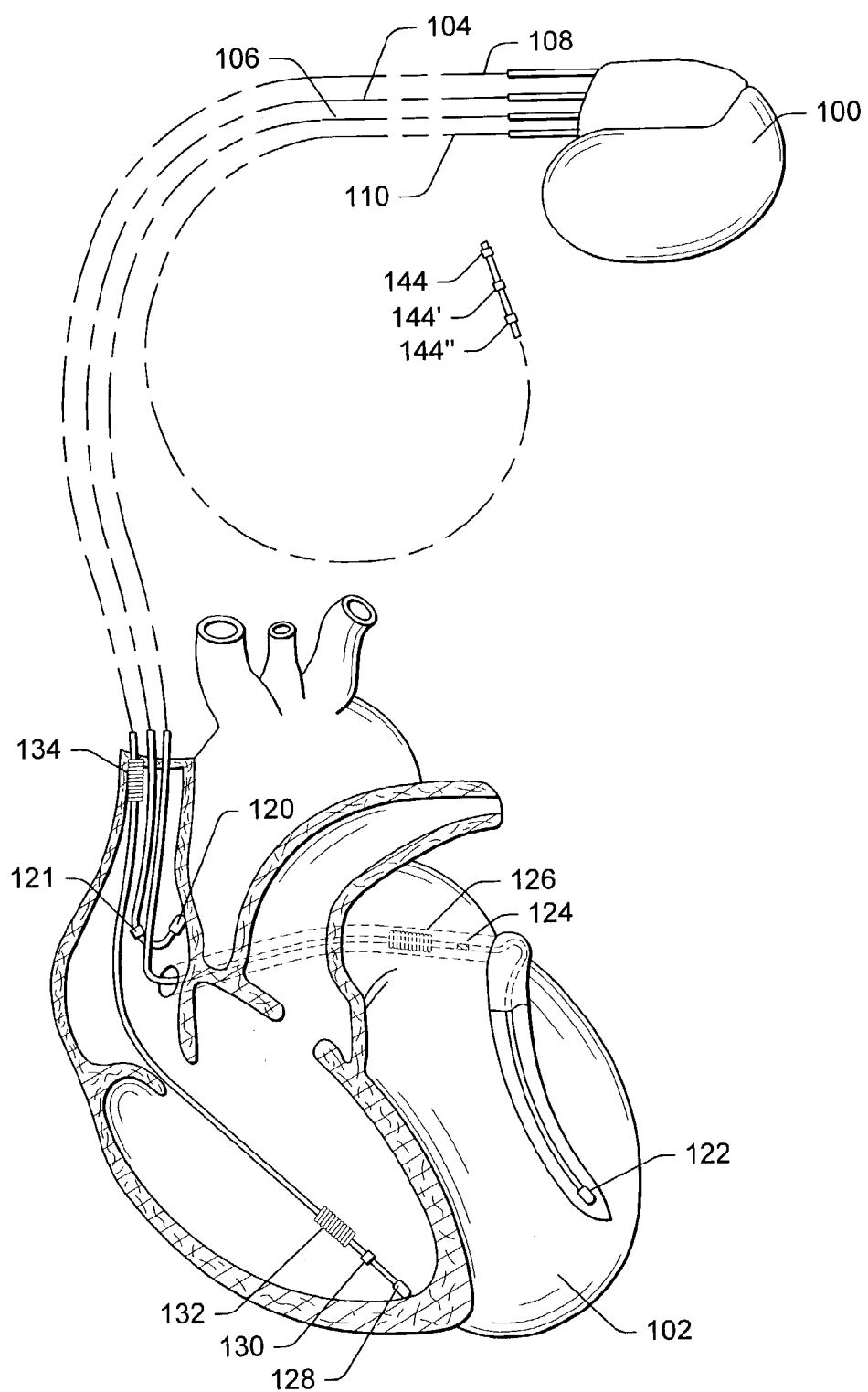
FIG. 1 is a simplified diagram illustrating an exemplary implantable stimulation device in electrical communication with at least three leads implanted into a patient's heart and at least one other lead for sensing and/or delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves and/or detection of other physiologic signals that may be used by the implanted system to modify the pacing parameters. This lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
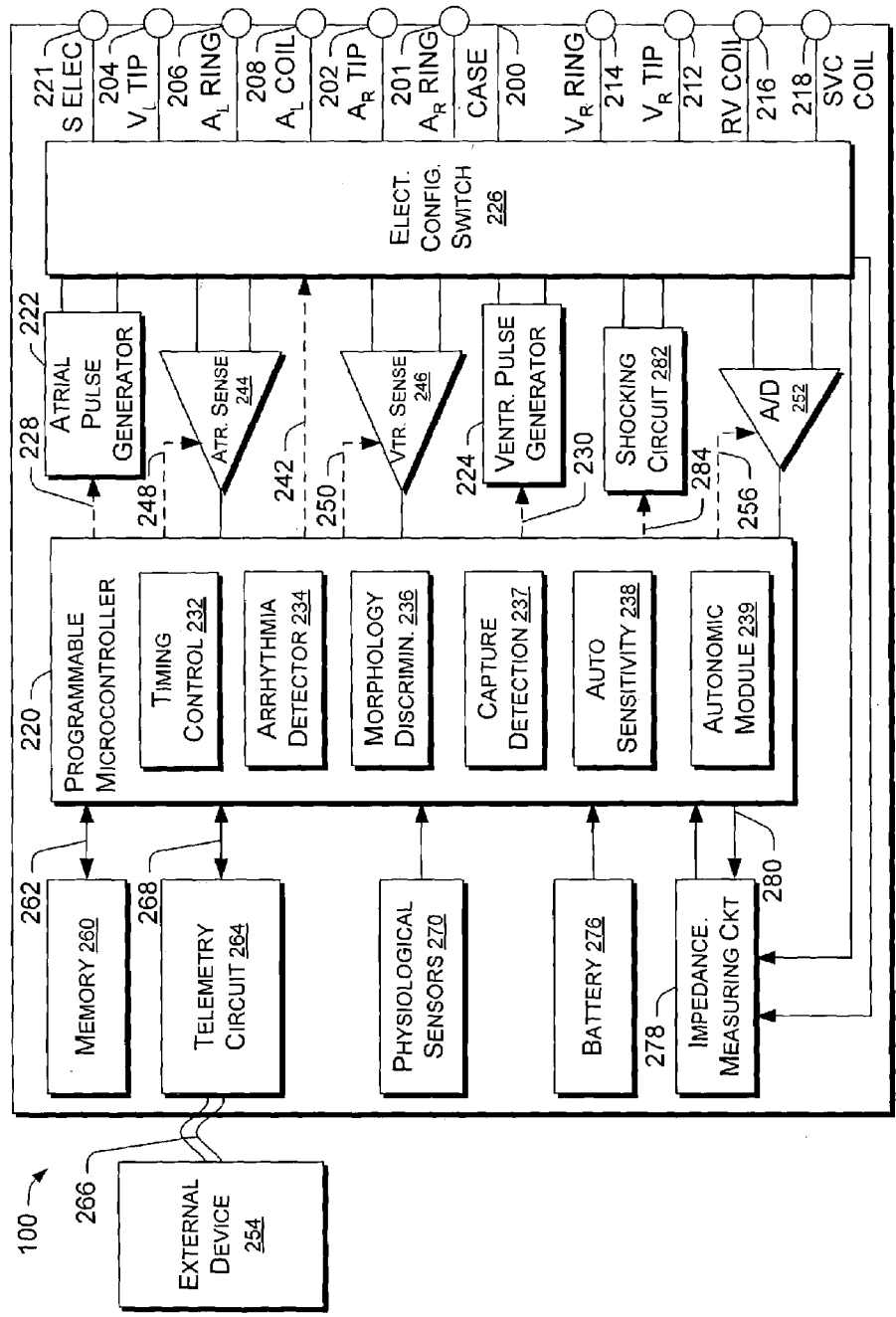
FIG. 2 is a functional block diagram of an exemplary implantable stimulation device illustrating basic elements that are configured to provide cardioversion, defibrillation, pacing stimulation and/or autonomic nerve stimulation or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal (AR TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (A—A) delay, or interventricular conduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234 and optionally an orthostatic compensator and a minute ventilation (MV) response module, the latter is not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation.

Microcontroller 220 further includes an autonomic nerve stimulation module 239 for performing a variety of tasks related to autonomic nerve stimulation. This component can be utilized by the stimulation device 100 for determining desirable times to administer various therapies, including, but not limited to, parasympathetic stimulation. The autonomic module 239 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 $\mu$A), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (up to 0.5 J), moderate (0.5 J to 10 J), or high energy (11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Heart Rhythm

Figure 3:
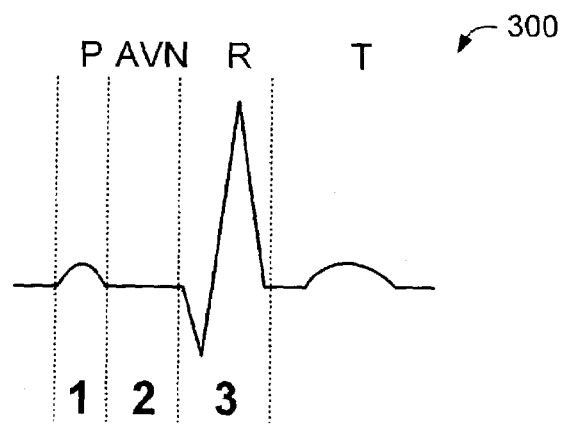
FIG. 3 is an approximate anatomical diagram of a heart and a waveform or ECG wherein the waveform includes a P wave and an R wave.
Figure 3:
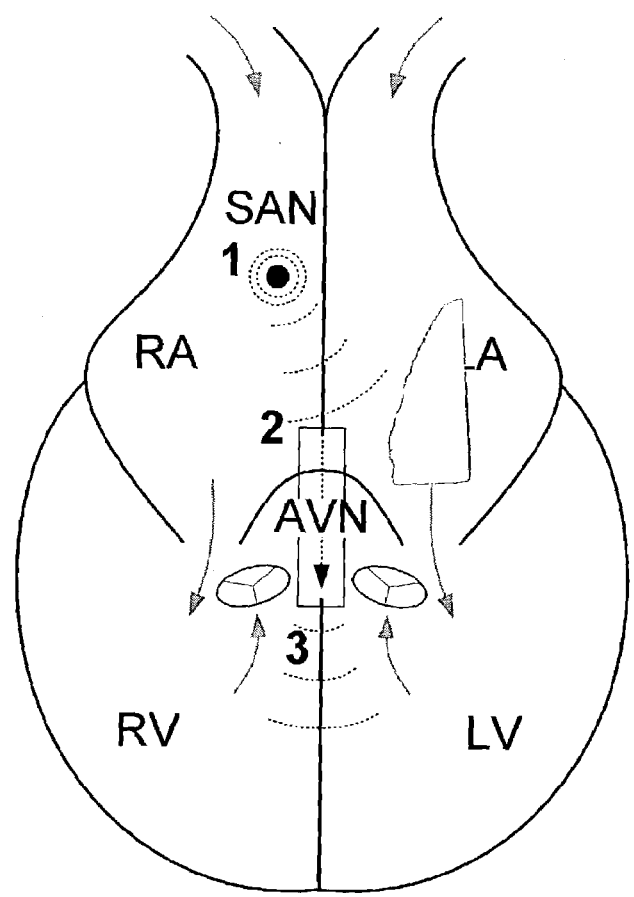

Referring to FIG. 3, an approximate anatomical diagram of a heart and a PR waveform 300 are shown. Action potentials propagating through a normal heart are labeled as follows: 1, associated with the sinoatrial node (SAN) and the atria; 2, associated with the atrioventricular node and/or atrioventricular bundle (AVN); and 3, associated with the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes ventricular contraction. Thus, in a normal heart, ventricular rhythm relies on intrinsic or native atrial action potentials and conduction of such action potentials through the AV node and AV bundle (collectively referred to as the AV node or AVN).

An electrocardiogram (ECG) of normal heart activity (e.g., polarization, depolarization, etc.) typically shows atrial depolarization as a "P wave", ventricular depolarization as an "R wave", or QRS complex, and repolarization as a "T wave".

Paced and/or Native Waveforms

Figure 4:
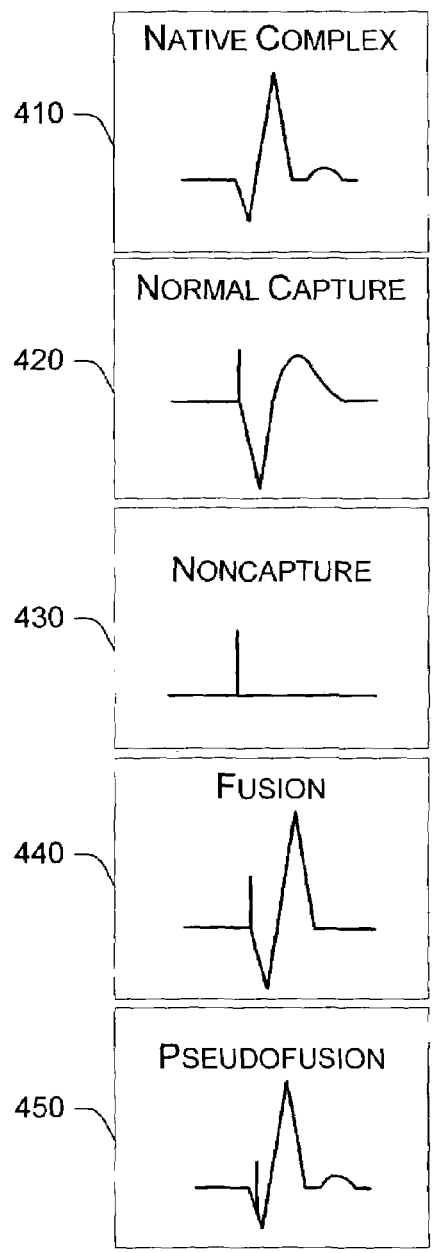
FIG. 4 is a diagram of various exemplary waveforms including native, capture, noncapture, fusion and pseudofusion.

Referring to FIG. 4, various exemplary waveforms 400 are shown. As discussed herein, a ventricular waveform caused by a ventricular stimulus is generally referred to as an evoked response while a ventricular waveform caused by a native stimulus (e.g., conducted SAN action) is generally referred to as an R wave or native QRS complex. The exemplary waveforms 400 include a native waveform 410 (e.g., per an ECG), which exhibits a distinct QRS complex and a distinct T wave. A paced ventricular waveform 420 that results in capture (i.e., an evoked response) differs from the native waveform 410. For example, a typical evoked response obscures repolarization; hence, the paced ventricular waveform 420 lacks a distinct T wave. If the ventricles are refractory or if the stimulus energy is insufficient, then a non-capture waveform results 430. The particular non-capture waveform 430 corresponds to a scenario lacking native or intrinsic activity; the stylized waveform exhibits a stimulus artifact only. Of course, intracardiac electrograms (IEGMs) acquired with use of a blanking interval may not exhibit such an artifact.

As discussed above, fusion is typically characterized by a wave complex formed by depolarization of the myocardium initiated by both a non-native stimulus and a native stimulus. As shown in FIG. 4, a fusion waveform 440 includes characteristics of a native waveform and a paced ventricular waveform. In particular, the waveform 440 includes depolarization due to an administered stimulus. In contrast, pseudofusion is typically characterized by a wave complex formed by depolarization of the myocardium initiated by a native stimulus; however, a non-native stimulus, that does not significantly contribute to depolarization, is present that distorts the wave complex. The exemplary waveforms 400 include a pseudofusion waveform 450, which exhibits a native waveform and a stimulus artifact wherein the stimulus does not significantly contribute to depolarization. As described herein, a waveform indicative of fusion may be referred to as a "fusion beat" and a waveform indicative of pseudofusion may be referred to as a "pseudofusion beat".

Fusion and Pseudofusion in Pacing Therapy

In traditional pacing systems, fusion and pseudofusion beats are typically inconsequential without adverse effects on a patient; although, such beats may result in some confusion on the part of the medical staff caring for the patient. In more advanced pacing systems, however, fusion and/or pseudofusion beats may seriously interfere with objectives of some algorithms and therapies. For example, an algorithm that detects capture may misinterpret a fusion waveform or a pseudofusion waveform as a loss of capture and, in response, deliver a back-up stimulus. In these scenarios, the back-up stimulus is unwarranted because native activity is present (i.e., native activity always accompanies fusion and pseudofusion). Further, delivery of an unwarranted back-up stimulus needlessly diminishes an implantable device's limited power supply.

Another pacing therapy that can benefit from recognition of fusion and pseudofusion is dual chamber pacing for management of hypertrophic obstructive cardiomyopathy (HOCM). HOCM pacing therapy typically relies on full ventricular capture, i.e., ventricular stimulus and ventricular capture prior to arrival of a native stimulus or a paced atrial stimulus. Thus, HOCM pacing algorithms often use a short AV interval to ensure delivery of the ventricular stimulus prior to arrival of any native or paced atrial stimuli. For example, an algorithm may sense an atrial event, commence an AV interval and then deliver a ventricular stimulus upon expiration of the AV interval. However, many HOCM patients have short baseline PR intervals; thus, to avoid fusion or pseudofusion an algorithm may implement a very short AV interval, indeed, possibly too short for effective atrial contraction and ventricular filling. In addition, some algorithms for management of HOCM also account for PR interval shortening associated with an increased intrinsic heart rate. Overall, in HOCM patients having adequate AV nodal conduction, if the AV interval is too long, the risk of fusion and pseudofusion increases and hence, so does the risk of inadequate ventricular action. Thus, fusion and/or pseudofusion may be counterproductive and compromise intended hemodynamic benefits. Consequently, exemplary recognition algorithms presented herein can improve HOCM therapy.

While fusion and pseudofusion avoidance can improve some pacing therapies, other pacing therapies can benefit from algorithms that help promote fusion. For example, some multisite pacing therapies for dilated cardiomyopathy and congestive heart failure actually rely on fusion because the resulting ventricular activation sequence provides the best hemodynamic results. Therefore, various exemplary fusion and/or pseudofusion recognition algorithms can enhance performance of particular pacing therapies.

Figure 5:
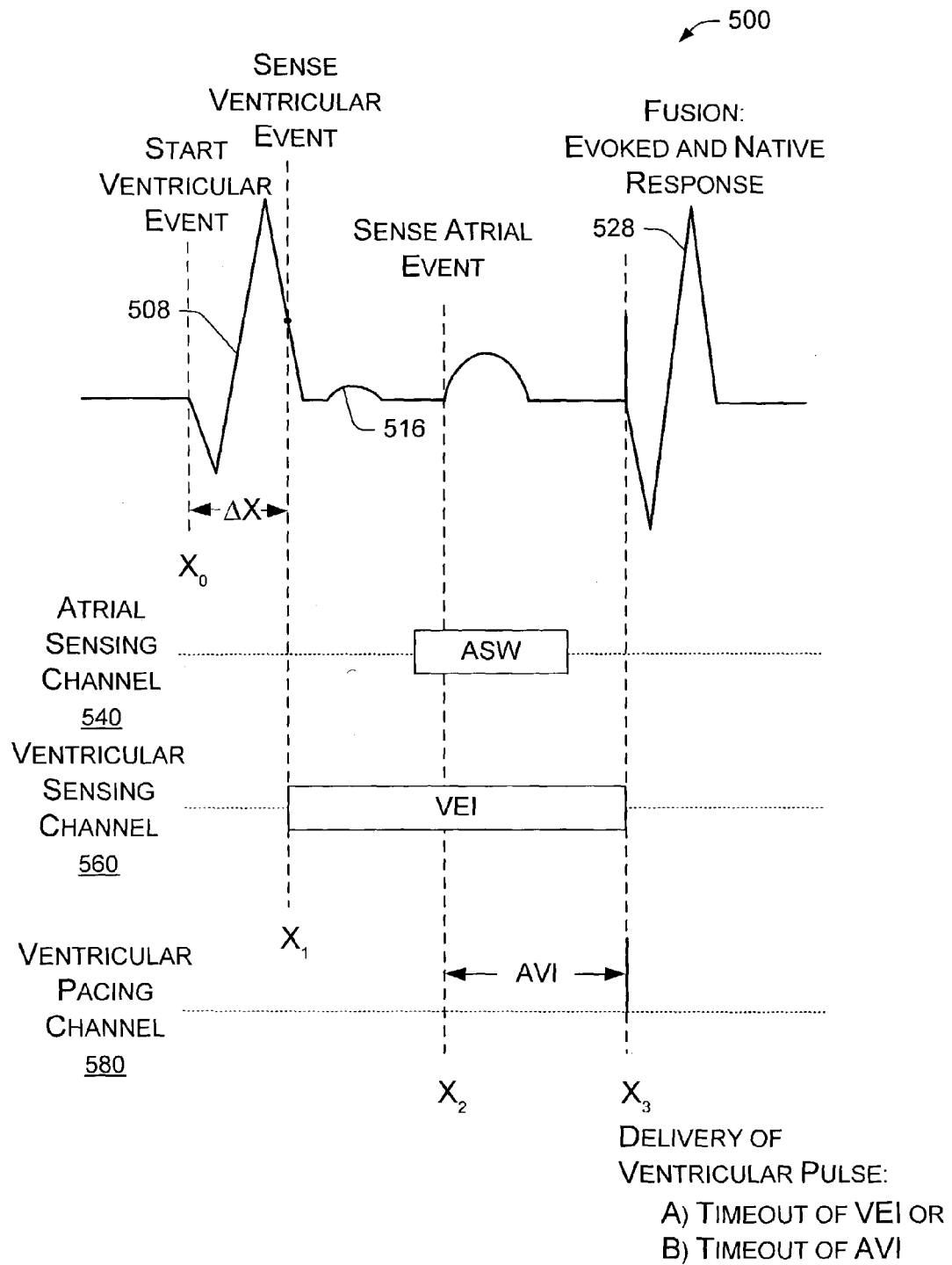
FIG. 5 is a diagram of an exemplary fusion scenario that includes waveforms and sensing and pacing channels.

To understand better the workings of various exemplary recognition algorithms, a brief discussion of fusion and pseudofusion follows wherein waveforms and sensing and delivery events are shown. FIG. 5 shows an exemplary fusion scenario 500 wherein an intrinsic ventricular event commences at time $X_0$ and produces waveform 508, which is sensed at time $X_1$. Note that a delay, $\Box X$, exists between commencement time $X_0$ and sensing or detection time $X_1$ of the intrinsic ventricular event. A ventricular sensing channel 560 shows a ventricular escape interval (VEI) that commences upon sensing or detection (e.g., time $X_1$) of the intrinsic ventricular event. The VEI is a period between a ventricular sensed event (e.g., at time $X_1$) and the next ventricular stimulus (provided that hysteresis is not programmed). In this scenario, the VEI corresponds to a window, wherein if no subsequent ventricular activity is detected, a ventricular stimulus occurs at the end of that timing period. In dual-chamber pacing, VEI may also be equivalent to a minimum rate, a lower rate interval, a lower rate limit or a base rate.

Referring again to the waveforms, a T wave 516 follows the sensing of the intrinsic ventricular event (e.g., at time $X_1$) and on an atrial sensing channel 540, an atrial sensing window commences for sensing an intrinsic atrial event (e.g., a P wave). As shown, at approximately time $X_2$, the atrial sensing channel 540 senses an atrial event during the atrial sensing window, which initiates a PV interval. In this example, a PV interval refers to an interval initiated by an intrinsic event whereas an AV interval refers to an interval initiated by a paced atrial stimulus. According to this exemplary scenario 500, if the ventricular sensing channel 560 fails to sense or detect an intrinsic ventricular event prior to timing out, or if the PV interval times out, then a ventricular stimulus is delivered, as indicated by an event at time $X_3$ on a ventricular pacing channel 580, which fuses with native activity to produce a fusion waveform 528. Fusion occurs in this exemplary scenario because the PV interval or the VEI were too long compared to the PR interval and/or because of the delay, $\Box X$, in ventricular event sensing or detection.

Figure 6:
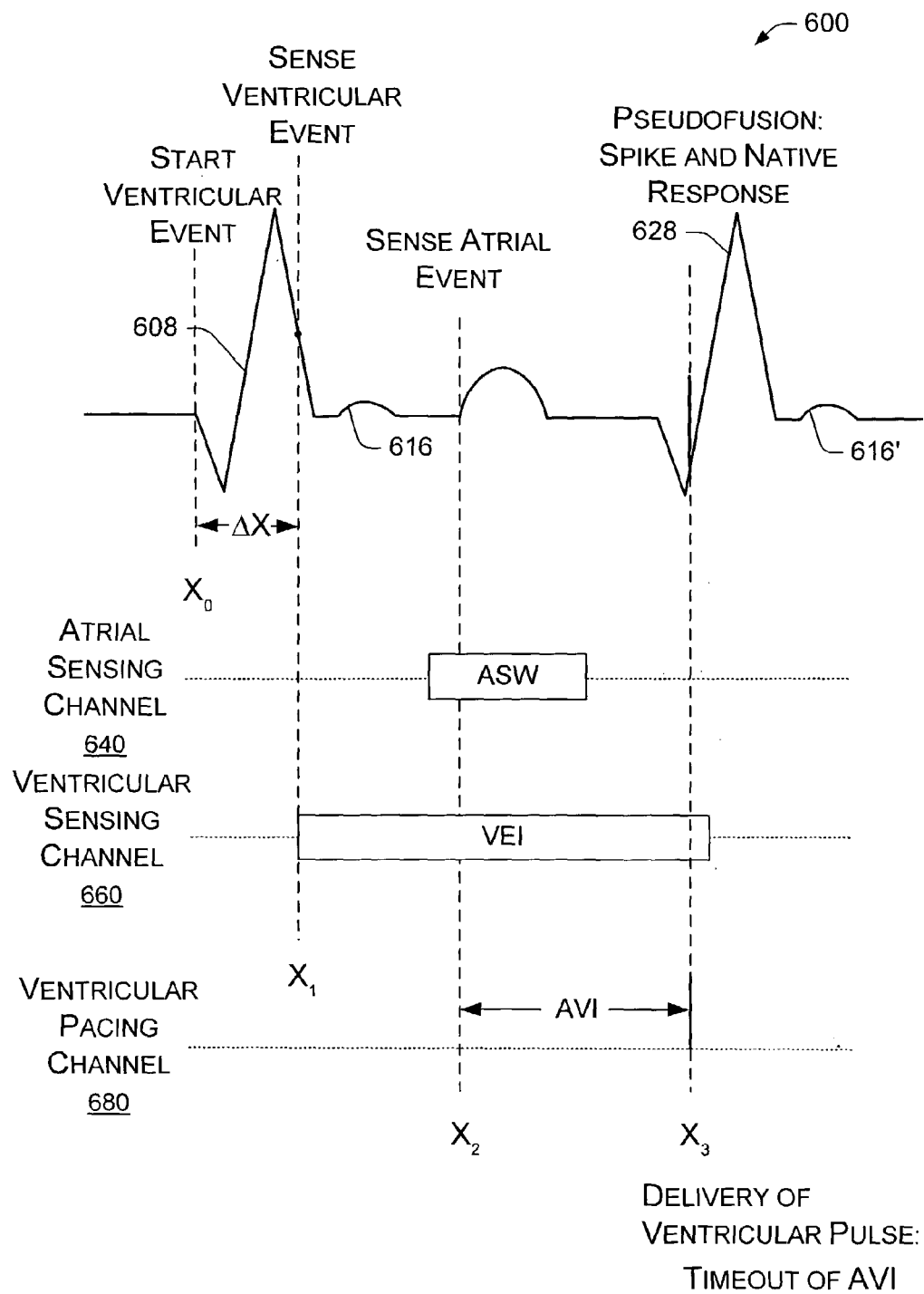
FIG. 6 is a diagram of an exemplary pseudofusion scenario that includes waveforms and sensing and pacing channels.

FIG. 6 shows an exemplary pseudofusion scenario 600. An intrinsic ventricular event commences at time $X_0$ and produces waveform 608, which is sensed at time $X_1$. Note that a delay, $\Box X$, exists between commencement time $X_0$ and sensing or detection time $X_1$ of the intrinsic ventricular event. A ventricular sensing channel 660 shows a ventricular escape interval (VEI) that commences upon sensing or detection (e.g., time $X_1$) of the intrinsic ventricular event. In this scenario, the VEI corresponds to a window following the last ventricular paced or sensed event, wherein if no subsequent ventricular is detected, a ventricular stimulus occurs. Referring again to the waveforms, a T wave 616 follows the sensing of the intrinsic ventricular event 612 and on an atrial sensing channel 640, an atrial sensing window commences for sensing an intrinsic atrial event (e.g., a P wave). As shown, at time $X_2$, the atrial sensing channel 640 senses an atrial event during the atrial sensing window, which initiates a PV interval. According to this exemplary scenario 600, if the ventricular sensing channel 660 fails to sense or detect an intrinsic ventricular event prior to the PV interval timing out, then a ventricular stimulus is delivered, as indicated by a ventricular pacing channel 680. The stimulus at time $X_3$ occurs during intrinsic activity to produce a waveform 628 having a superimposed stimulus (i.e., a pseudofusion waveform). In this scenario a T repolarization wave 616' follows the pseudofusion waveform. Psuedofusion occurs in this exemplary scenario because the PV interval was too long compared to the PR interval and/or because of the delay, $\Box X$, in ventricular event sensing or detection.

Recognition of Fusion and/or Pseudofusion

Algorithms that recognize fusion and/or pseudofusion can (i) aid therapies that can be misled by the presence of fusion and/or pseudofusion beats; (ii) optimize hemodynamics that may be compromised or enhanced by fusion; (iii) reduce incidence of back-up pulses; and/or (iv) learn to avoid fusion and/or pseudofusion. Exemplary recognition algorithms presented herein rely on one of two approaches: capture detection and morphology discrimination or capture detection and auto sensitivity. A description of capture detection, morphology discrimination and auto sensitivity are given below followed by a description of exemplary recognition algorithms.

Capture Detection

Figure 7:
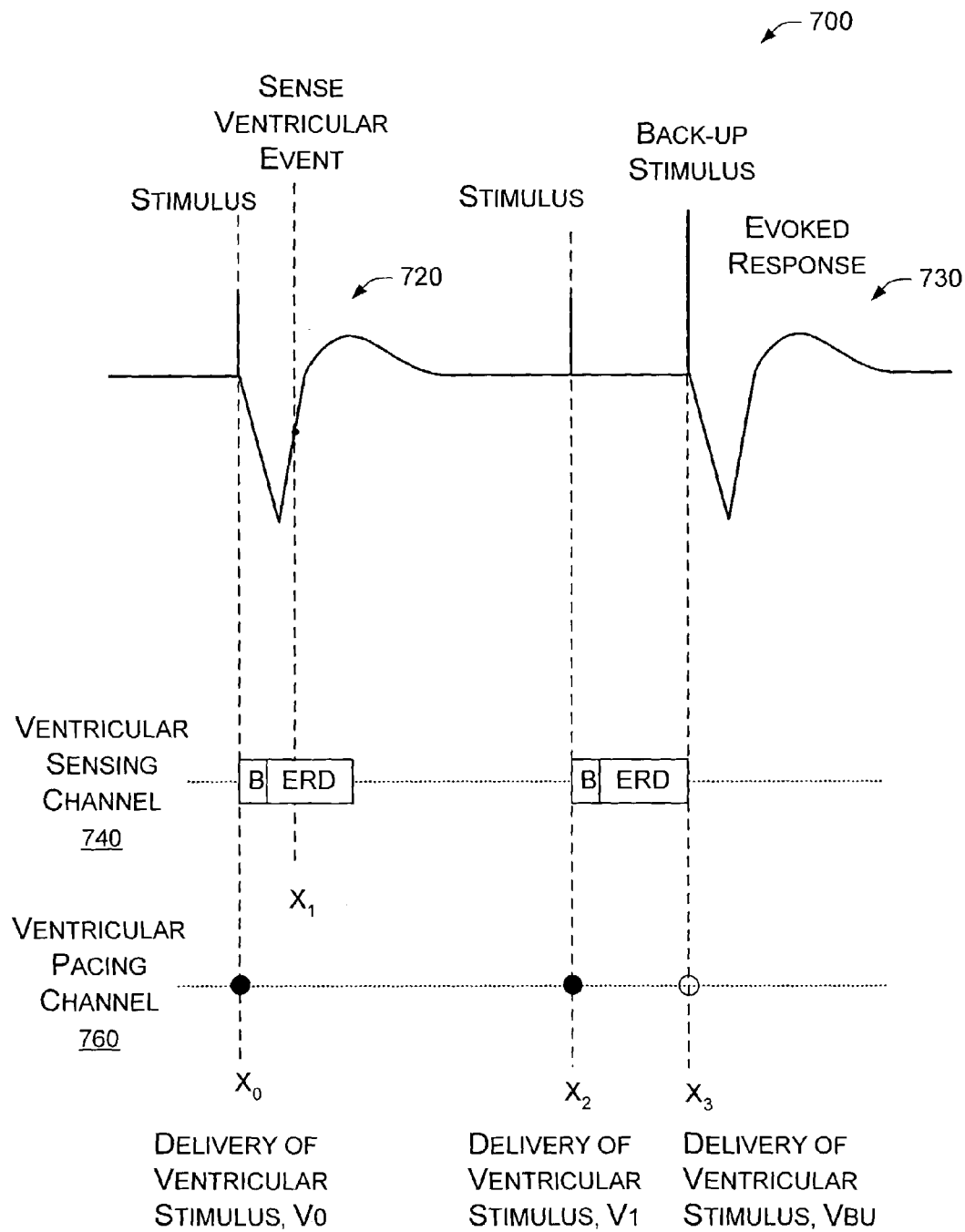
FIG. 7 is a diagram of an exemplary capture detection scenario that includes waveforms and sensing and pacing channels.

FIG. 7 shows a capture detection scenario 700. Capture detection aims to verify capture following a delivered stimulus. At a time $X_0$, a stimulus having amplitude $V_0$ is delivered per a ventricular pacing channel 760. At approximately this time, a ventricular sensing channel 740 initiates a blanking interval, B, during which no sensing occurs. Following the blanking interval, the ventricular sensing channel initiates an evoked response detection window, ERD, during which sensing of cardiac activity occurs. At a time $X_1$, the sensing channel 740 senses an evoked response 720; thus, verifying that the delivered stimulus resulted in successful capture.

Often, capture detection is used to determine a suitable stimulus energy level, for example, one that results in capture while minimizing drain on a device's limited power supply. Xo determine a suitable stimulus energy level, a device may deliver a stimulus at a lesser energy level following detection of a successful capture. At time $X_2$, the exemplary scenario 700 shows delivery of a stimulus having a lesser amplitude, $V_1$ (e.g., $|V_1|<|V_0|$), on the ventricular pacing channel 760. As in the prior cycle, the ventricular sensing channel 740 initiates a blanking interval, B, followed by an evoked response detection window, ERD. In this instance, however, the stimulus at time $X_2$ has insufficient energy; hence, it does not cause an evoked response and the evoked response detection window times out at a time of approximately $X_3$. As shown by the open circle on the ventricular pacing channel 760, the time out of the ERD initiates delivery of a back-up stimulus having amplitude $V_{BU}$ (e.g., where $|V_{BU}|>|V_0|$), which causes an evoked response 730. In general, the back-up stimulus amplitude $V_{BU}$ is chosen to ensure capture.

As already mentioned, devices that implement autocapture routines may misinterpret fusion and/or pseudofusion waveforms as noncapture or loss of capture and, in response thereto, deliver an unnecessary back-up stimulus. Misinterpretation may occur due to sensing and/or detection parameters associated with the evoked response detection window and/or the blanking interval.

Morphology Discrimination

Morphology discrimination typically relies on "dynamic template matching" to discriminate between normal and abnormal events (e.g., atrial and ventricular tachyarrhythmias), which may be present in sensed cardiac activity. Morphology discrimination enables a device to examine multiple characteristics of an electrogram (e.g., sensed cardiac activity), as opposed to techniques which may look only at a complex's width, amplitude and/or slew rate. Morphology discrimination allows for a comparison between a complex, or portion thereof, and a template. For example, morphology discrimination may compare a last acquired complex with a predetermined physician-selected patient-specific template. Morphology discrimination finds use in ICD patients who experience atrial tachyarrhythmias, providing them with an extra level of protection against unnecessary shocks that can occur when atrial tachyarrhythmias are mistaken for ventricular tachycardias. Morphology discrimination is optionally used in conjunction with other enhanced discrimination capabilities (e.g., sudden onset, interval stability, etc.) to provide a more effective complement of tools to improve discrimination of tachycardias (e.g., supraventricular tachycardias, etc.). In commercially available implementations of morphology discrimination, a MD algorithm is normally disabled in the setting of a delivered output pulse. In contrast, various exemplary methods described herein allow for morphology discrimination or other signal characterization following delivery of an output pulse. In particular, various exemplary methods allow for detection of characteristics that suggest depolarization is present even when a conventional evoked response sensing scheme indicates otherwise (e.g., using a standard evoked response sense amplifier and associated algorithm, etc.).

Some morphology discrimination techniques allow for automatic template update whereby a periodic evaluation of a stored template occurs followed by an update, which may be needed, for example, to accommodate changes in a patient's rhythm and/or signal characteristics. These techniques allow for modification of a template and/or replacement of a template based on sensed cardiac activity.

Figure 8:
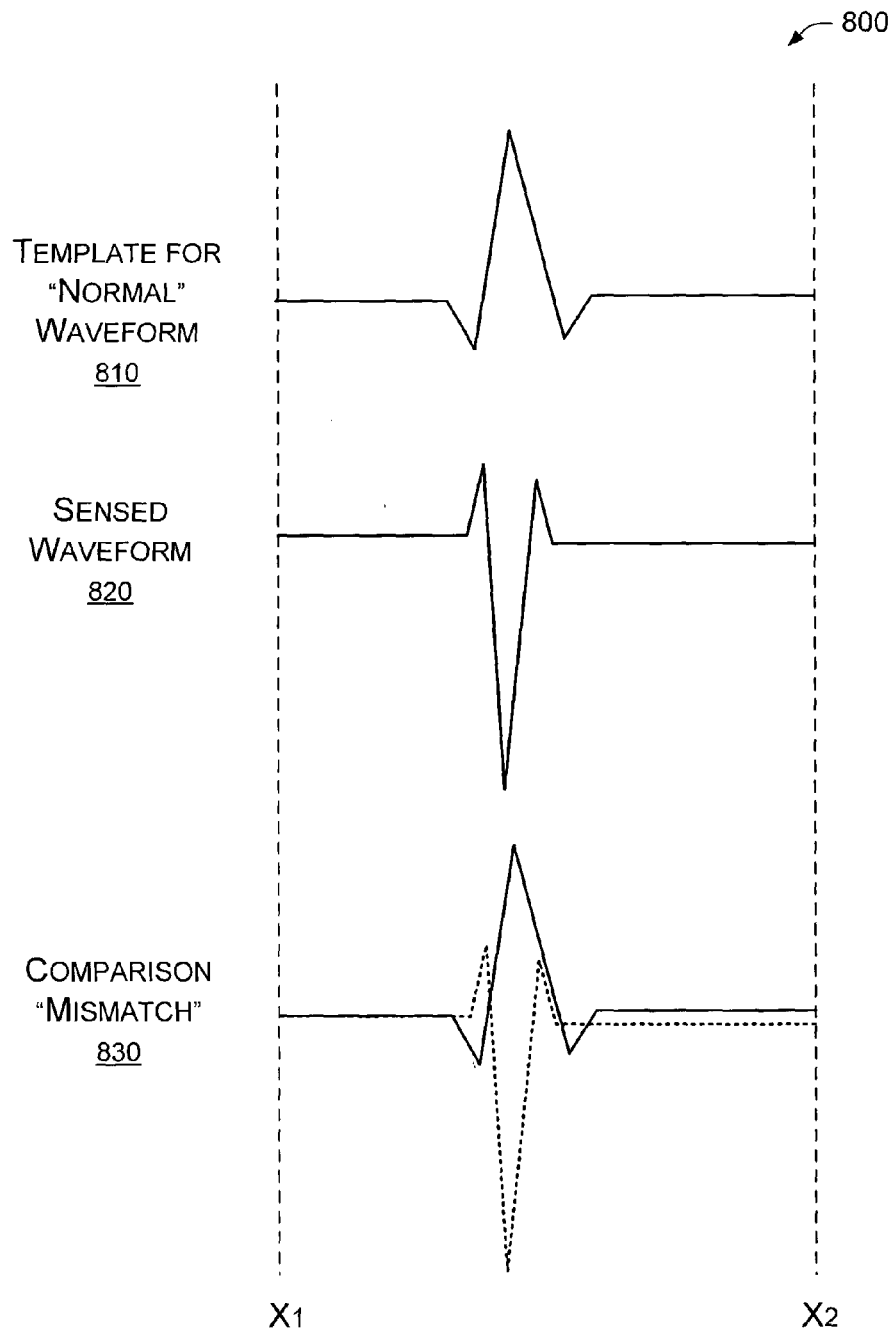
FIG. 8 is a diagram of an exemplary morphology discrimination scenario that includes a sensed waveform and a template.

FIG. 8 shows an exemplary morphology detection scenario 800 that includes a template 810 for a "normal" waveform and a sensed waveform 820. In this scenario, the template 810 and the waveform 820 have corresponding time bounds $X_1$ and $X_2$. Morphology discrimination may compare any portion of the sensed waveform 820 with the template 810. A comparison 830 shows that the sensed waveform 820 deviates significantly from the template 810 at various points within the bounds $X_1$ and $X_2$.

Autosensitivity

In general, an auto sensitivity algorithm adjusts one or more threshold values to improve sensing, detecting and/or responding. For example, an exemplary auto sensitivity algorithm may adjust a sensing, detecting and/or response threshold value upon detection of an R wave or other event. The algorithm may further adjust the threshold value during and/or after an R-T interval (e.g., as a function of time, upon detection of a T wave, etc.). An exemplary algorithm may adjust a threshold value after detection of a T wave to improve sensitivity of subsequent R wave detection. Often, an adjusted threshold value acts to limit sensing of noise, improper detecting due to noise, and/or responding to noise. For example, auto sensing can reduce over-sensing of and/or inappropriate responding to T waves and/or far-field R waves.

An exemplary auto sensitivity algorithm may also use cardiac event information (e.g., cardiac activity) to determine an interval between R wave events and T wave events (e.g., an R-T interval) and selectively adjust a sensing and/or response threshold value based on the R-T interval and/or additional sensed cardiac event information. Cardiac event information may include statistical information associated with a plurality of cardiac events, such as, average R and T wave amplitudes, an average R-T interval, etc.

Figure 9:
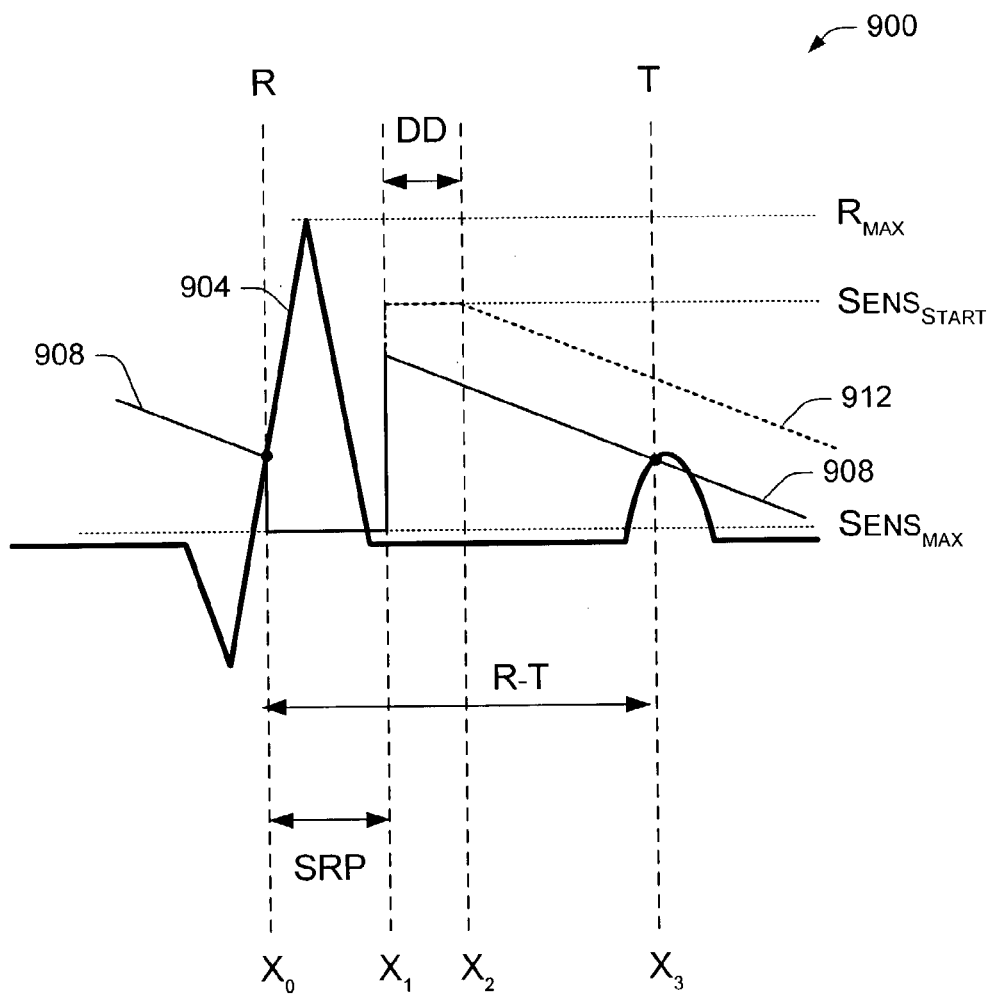
FIG. 9 is a diagram of an exemplary auto sensitivity scenario that includes waveforms and sensitivity levels.

FIG. 9 shows an exemplary auto sensitivity scenario 900 that includes a QRS-T complex. The scenario 900 includes a sense refractory period (SRP), which is an interval or timing cycle following a sensed or paced event during which a sense amplifier senses but does not allow a response (e.g., delivery of a stimulus, reset of a timing cycle, etc.) to sensed information whereas, in contrast, a blanking period temporarily disables a sense amplifier whereby the sense amplifier will not respond at all to incoming signals. The sense refractory period (SRP) commences at time $X_0$ wherein detection of, for example, an R wave of a QRS complex occurs. The SRP terminates at time $X_1$ either by timing out or by inactivity. Note that during the SRP, sensitivity 908 is set to the maximum sensitivity (Sens.$_{max}$), which corresponds to a smaller potential value (e.g., a potential value in mV) that allows for sensing of signals, for example, having potentials of at least the set potential value. Of course, a lesser sensitivity (i.e., greater potential value) may also be implemented.

Once the SRP times out, the sensitivity 908 is decreased (e.g., an increase to a higher potential value). The decrease may occur based on the maximum amplitude sensed during the SRP (e.g., $R_{max}$) or according to another scheme. In the scenario 900, sensitivity 912 corresponds to setting sensitivity to Sens.$_{start}$, which is optionally a percentage of $R_{max}$, while the sensitivity 908 corresponds to another scheme that initially decreases the sensitivity (e.g., an increase to a higher potential value) and then increases the sensitivity (e.g., a decrease to a lower potential value). According to such schemes, an increase in sensitivity means that smaller signals can be detected. Sensitivity is typically programmed in terms of the amplitude of the smallest signal that can be detected. Hence, a 1 mV sensitivity setting is a higher sensitivity than a 2 mV setting. At a 1 mV setting, a sensing system is more sensitive when compared to a 2 mV setting. By the same token, where less sensitivity or decreased sensitivity is desired, a programmable sensitivity is typically programmed to a higher potential value (e.g., a higher value in mV, etc.). Amplitude for an R wave is more straightforward wherein, for example, $R_{max}$ would typically represent the largest desirable signal for sensing.

The sensitivity 912 further implements a decay delay (DD), which acts to maintain the decreased sensitivity for a period of time; whereas, the sensitivity 908 begins an immediate decay at the end of the SRP. Note that in this scenario, the sensitivity 908 approaches the maximum sensitivity Sens.$_{max}$ at the same rate as the sensitivity 912; however, due to the initial offsets, the sensitivity 908 will reach the maximum sensitivity Sens.$_{max}$ sooner. The offset for the sensitivity 912 allows for non-sensing of T waves and other known but inappropriate low amplitude signals that may otherwise be sensed at a very sensitive setting. As such, a scheme that uses the sensitivity 908 may detect T wave activity whereas a scheme that uses the sensitivity 912 has less of a chance of detecting T wave activity. The decay delay, slope of decay and/or other sensitivity parameter(s) are optionally set based, in part, on an R-T interval, which spans times $X_0$ to $X_3$. As mentioned above, auto sensing may include techniques to determine or measure an R-T interval. Further, appropriate selection of auto sensing parameters is optionally based on measured amplitude of previously sensed events, type of cardiac cycle (paced or sensed), measurement of the current myopotential/environmental noise level, etc. Various exemplary methods described herein any activity sensed immediately after delivery of a pacing stimulus may be used in deciding whether fusion and/or pseudofusion may have occurred and consequently may be used to alter or adjust pacing therapy. Of course, if activity is sensed prior to delivery of such a pacing stimulus, inhibition of the pacing stimulus typically occurs.

Capture Detection and Morphology Discrimination

An exemplary fusion and/or pseudofusion recognition algorithm uses capture detection and morphology discrimination features. Morphology discrimination includes comparing sensed cardiac activity to a template (e.g., characteristic of native activity, etc.). Morphology discrimination is normally disabled with delivery of a pacing stimulus. According to various exemplary methods described herein, morphology discrimination remains active following delivery of a pacing stimulus to evaluate the morphology of any complex occurring at any time after delivery of a stimulus. For example, morphology discrimination may rely on (i) cardiac activity sensed after expiration of an evoked response window, and/or (ii) cardiac activity sensed in a specific morphology detection window. In the latter case, the morphology detection window optionally commences during an evoked response detection window. The morphology detection circuitry may utilize different filters and amplifiers than conventional evoked response detection circuitry.

According to various exemplary recognition algorithms, if a capture detection feature recognizes capture (i.e., that a delivered stimulus resulted in capture), then morphology discrimination is not implemented. However, if the capture detection feature makes a determination of non-capture, then morphology discrimination is implemented. Again, morphology discrimination typically relies on a template characteristic of a native waveform or activity; of course, templates characteristic of fusion and/or pseudofusion may also be used.

In general, morphology discrimination compares one or more portions of sensed cardiac activity to appropriate corresponding portions of a template. If an adequate match exists between the compared portions, then the morphology discrimination feature determines that the sensed activity includes, for example, native activity. Consequently, the initial non-capture determination is reclassified as fusion and/or pseudofusion. Such a reclassification may cause an implantable stimulation device to withhold delivery of a back-up stimulus and thereby prolong longevity of the device's limited power supply. It may also cause a stimulation device to withhold AV interval extension in accord with any particular implementation of conventional fusion avoidance algorithms.

An exemplary recognition algorithm that relies on morphology discrimination may also further differentiate fusion and pseudofusion. As explained with reference to FIG. 4, fusion and pseudofusion typically exhibit different native characteristics. In general, a pseudofusion waveform retains more native waveform characteristics than does a fusion waveform. Consequently, if a sensed waveform has few native characteristics, then the sensed waveform is more likely to be due to a fusion beat. Such an algorithm uses one or more selected portions of a native waveform template to differentiate fusion and pseudofusion waveforms. For example, if latter components of the sensed waveform match latter components of the native template, then the sensed waveform would correspond to a pseudofusion beat. Whereas, if the latter components differ, the complex would correspond to a fusion beat.

An exemplary recognition algorithm may restrict a morphology discrimination comparison to cardiac activity that occurs after expiration of a capture or evoked response detection (ERD) window and prior to delivery of a prospective back-up stimulus. In this example, sensing would occur between expiration of an ERD and delivery of a prospective back-up stimulus (which differs from the scenario 700 shown in FIG. 7). If significant cardiac activity is sensed (e.g., activity above a noise, a sensing, a detection and/or a response threshold, etc.) in this interval, then the delivered stimulus resulted in a fusion or pseudofusion beat. After such a determination, the exemplary algorithm may cause a device to withhold delivery of a back-up stimulus. Other options include recording the number of fusion beats and/or pseudofusion beats in a diagnostic event counter, which may be analyzed to provide further therapeutic benefit.

Figure 10:
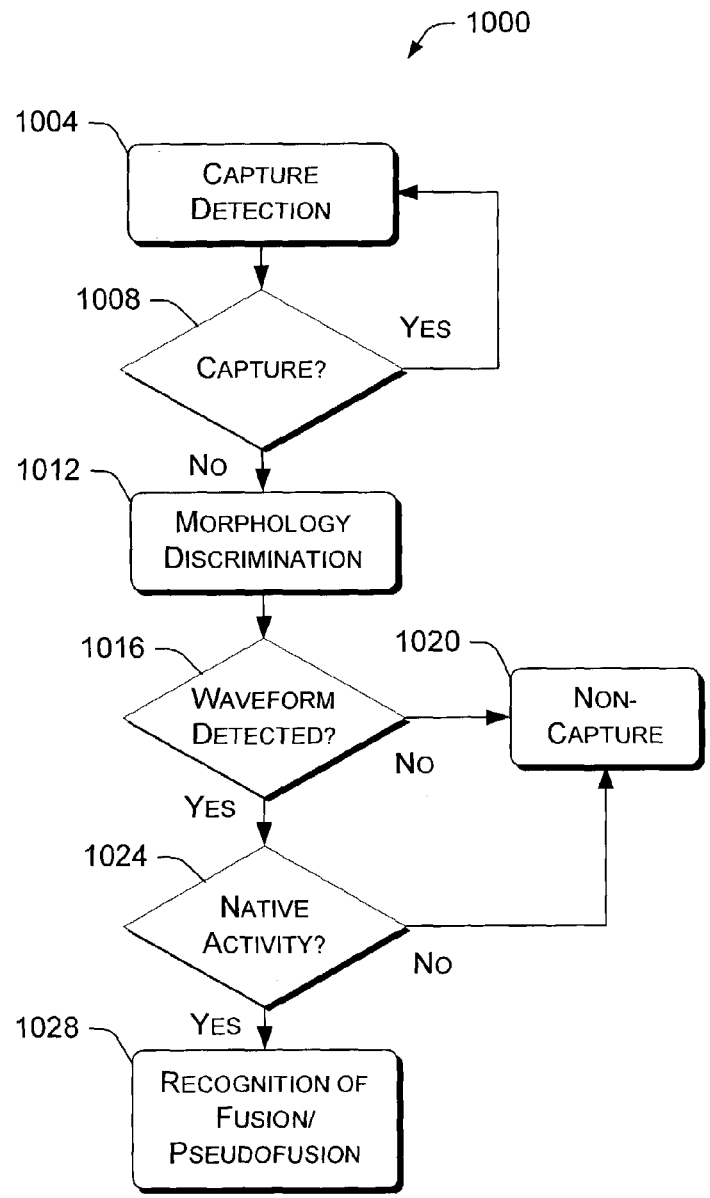
FIG. 10 is a block diagram of an exemplary method for recognizing fusion and/or pseudofusion that includes capture detection and morphology discrimination features.

FIG. 10 shows an exemplary method 1000 for recognition of fusion and/or pseudofusion. The exemplary method 1000 commences in a stimulus delivery block 1004, which causes delivery of a stimulus to cardiac tissue. Following the delivery, in a sense cardiac activity block 1008, sensing of cardiac activity occurs. Typically, during or after sensing, a decision block 1012 makes an initial determination as to whether the delivered stimulus resulted in capture. This determination may rely on techniques used in traditional capture detection algorithms (e.g., autocapture, etc.). If the decision block 1012 determines that capture occurred, then the method 1000 continues in the delivery block 1004. Of course other suitable action may occur (e.g., setting of a stimulus threshold, etc.). However, if the decision block 1012 determines that capture did not occur (i.e., non-capture), then the method 1000 continues in another decision block 1016.

According to this exemplary method 1000, the decision block 1016 determines if any significant cardiac activity or waveform was sensed in the sensing block 1008 (e.g., activity above a noise, a sensing, a detection and/or a response threshold, etc.). If the decision block 1016 determines that no significant activity was sensed, then it is unlikely that native activity was present following the stimulus, and hence, the non-capture determination is verified in a verification block 1020. If significant cardiac activity exists, then the method 1000 continues in a morphology discrimination block 1024 which makes a comparison between sensed activity and a template. As mentioned above, sensed activity may be activity sensed during the sensing associated with capture detection and/or activity sensed in a morphology discrimination window or at some other suitable time. In all of these scenarios, the relevant sensed cardiac activity is compared to a template, for example, a template characteristic of native activity. A decision block 1028 then follows the morphology discrimination comparison which makes a determination as to the presence of native activity. If the decision block 1028 determines that the sensed activity includes no characteristics of native activity, then the method 1000 continues in the non-capture verification block 1020. However, if characteristics of native activity are present, then the method 1000 continues in a fusion and/or pseudofusion recognition block 1032, which recognizes that the delivered stimulus resulted in a fusion or pseudofusion beat. Appropriate next steps may follow, such as, but not limited to, withholding of a back-up stimulus and/or further characterization of the sensed waveform as fusion or pseudofusion.

Various exemplary methods that rely on capture detection and morphology discrimination are suitable for recognizing ventricular fusion and/or pseudofusion. Accordingly, a stimulus may be a ventricular stimulus and sensed cardiac activity may be sensed ventricular activity. Of course, various exemplary methods may be suitable for recognizing atrial fusion and/or pseudofusion.

Capture Detection and Auto Sensitivity

An exemplary fusion and/or pseudofusion recognition algorithm uses capture detection and auto sensitivity features. If a capture detection feature recognizes capture, the auto sensitivity feature is not implemented. However, if the capture detection feature makes an initial determination of non-capture, then the auto sensitivity feature is implemented. Auto sensitivity is typically based on detection of native events. An exemplary recognition algorithm may enable auto sensitivity following delivery of a stimulus and have capabilities to recognize various components of a sensed waveform (e.g., cardiac depolarization). According to such an algorithm, after an initial determination of non-capture, the algorithm adjusts sensitivity to enhance sensing of native activity. If native activity is sensed, then the initial determination of non-capture is reclassified as fusion or pseudofusion. Such an exemplary algorithm may sense a portion of a waveform or sense an entire waveform. In addition, it may rely on an entire sensed waveform or one or more portions of a sensed waveform.

An exemplary recognition algorithm optionally adjusts sensitivity to sense additional components of a waveform that might be present between a period defined by the end of a capture or evoked response detection (ERD) window and a projected delivery time for a back-up stimulus. Note that in this example, a delay would exist between the ERD and the prospective back-up stimulus (which differs from the scenario 700 shown in FIG. 7). If components of a waveform are sensed during this time period, it would establish that the initial non-capture determination was faulty, in that, fusion or pseudofusion occurred. This exemplary algorithm would then recognize that native activity occurred prior to and/or during delivery of the stimulus and optionally withhold delivery of a back-up stimulus. Other options include recording the number of fusion beats and/or pseudofusion beats in a diagnostic event counter, which may be analyzed to provide further therapeutic benefit.

Figure 11:
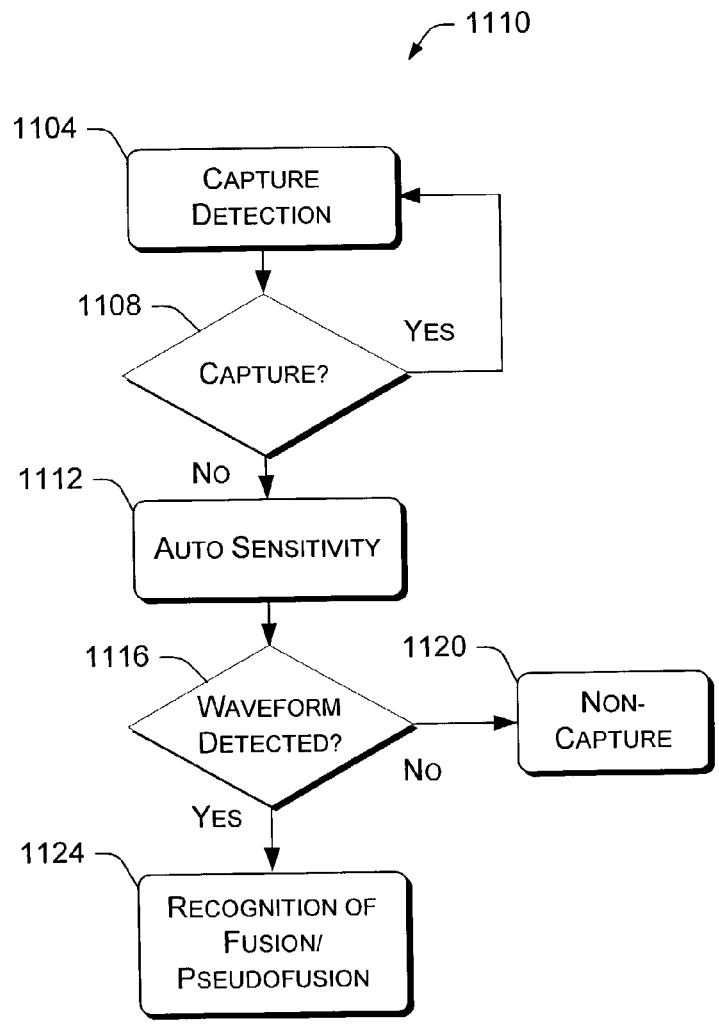
FIG. 11 is a block diagram of an exemplary method for recognizing fusion and/or pseudofusion that includes capture detection and auto sensitivity features.

FIG. 11 shows an exemplary method 1100 for recognition of fusion and/or pseudofusion. The exemplary method 1100 commences in a stimulus delivery block 1104, which causes delivery of a stimulus to cardiac tissue. Following the delivery, in a sense cardiac activity block 1108, sensing of cardiac activity occurs. Typically, during or after sensing, a decision block 1112 makes an initial determination as to whether the delivered stimulus resulted in capture. This determination may rely on techniques used in traditional capture detection algorithms (e.g., autocapture, etc.). If the decision block 1112 determines that capture occurred, then the method 1100 continues in the delivery block 1104. Of course other suitable action may occur (e.g., setting of a stimulus threshold, etc.). However, if the decision block 1112 determines that capture did not occur (i.e., non-capture), then the method 1100 continues in an auto sensitivity block 1016.

The auto sensitivity block 1116 aims to adjust sensitivity to enhance sensing of any native activity that may be present after the initial non-capture determination. After and/or during an enhanced sensing period initiated by the auto sensitivity block 1116, a decision block 1120 determines if any significant cardiac activity was sensed (e.g., activity above a noise, a sensing, a detection and/or a response threshold, etc.). If the decision block 1120 determines that no significant cardiac activity was sensed, then the method 1100 continues in a non-capture verification block 1124. However, if a significant cardiac activity was sensed, then the method 1100 continues in a fusion and/or pseudofusion recognition block 1128. Appropriate next steps may follow, such as, but not limited to, withholding of a back-up stimulus and/or further characterization of the sensed waveform as fusion or pseudofusion.

An exemplary recognition algorithm may implement auto sensitivity immediately following delivery of a stimulus in an autocapture scenario. In this example, the auto sensitivity feature would increase sensitivity after a blanking interval to enhance sensing and the autocapture algorithm would rely on a traditional evoked response detection scheme to make an initial determination as to whether capture occurred. For example, the autocapture algorithm may rely on a technique that uses a threshold and/or a slope to detect capture while more detailed information acquired due to enhanced sensing would only be used if the detection technique indicated non-capture. Again, if the enhanced sensing does not sense any significant activity, then non-capture is verified. In addition, enhanced and/or adjustable sensing may occur even after expiration of the autocapture algorithm's evoked response detection window.

Various exemplary methods that rely on capture detection and auto sensitivity are suitable for recognizing ventricular fusion and/or pseudofusion. Accordingly, a stimulus may be a ventricular stimulus and sensing of cardiac activity may pertain to ventricular activity. Of course, various exemplary methods may be suitable for recognizing atrial fusion and/or pseudofusion.

Capture Detection, Morphology Discrimination and Auto Sensitivity

Figure 12:
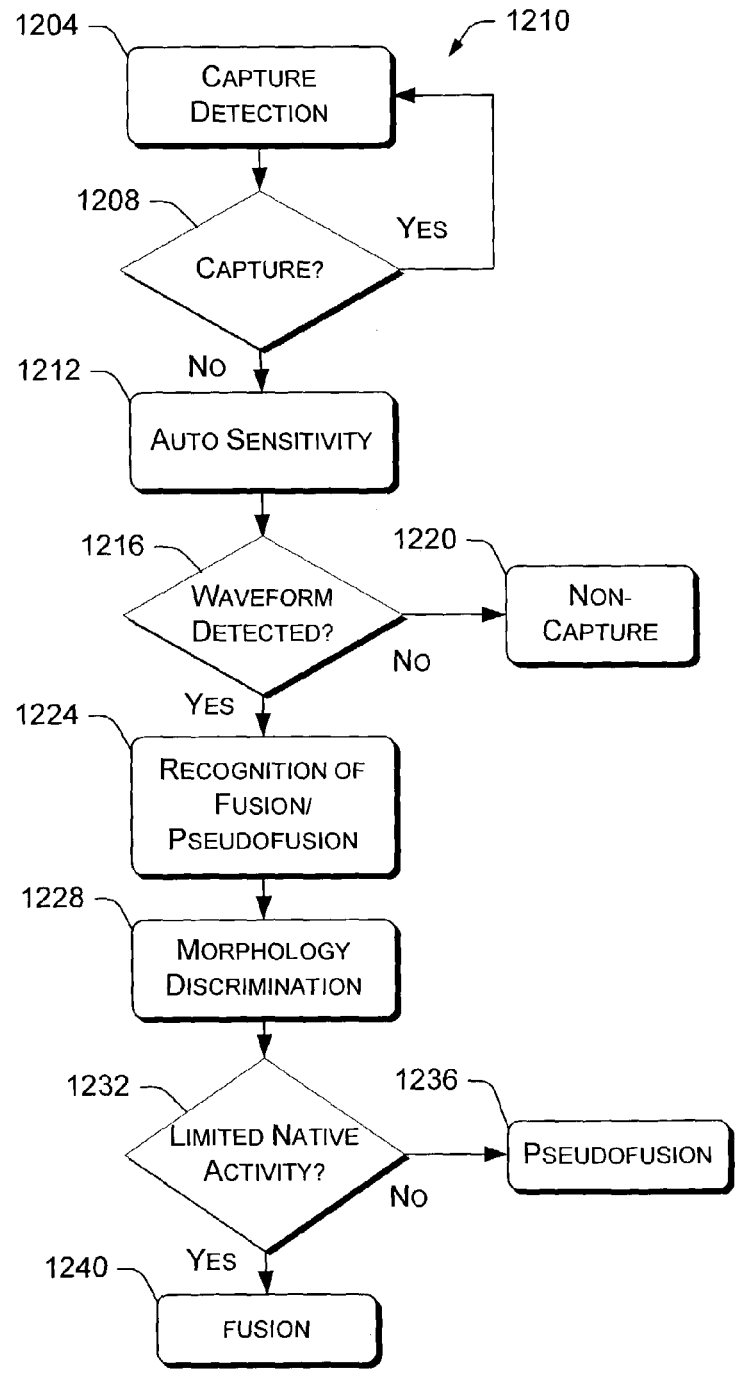
FIG. 12 is a block diagram of an exemplary method for recognizing fusion and/or pseudofusion that includes capture detection, auto sensitivity and morphology discrimination features.

An exemplary recognition algorithm uses capture detection and morphology discrimination in conjunction with auto sensitivity. FIG. 12 shows an exemplary method 1200 for recognition of fusion and/or pseudofusion. The exemplary method 1200 commences in a delivery/sense block 1204, which uses, for example, capture detection features for delivery of a stimulus and sensing of an evoked response. A decision block 1208 follows which uses a capture detection feature to help determine if the delivered stimulus resulted in capture. If the decision block 1208 determines that capture occurred, then the method 1200 optionally continues in the delivery/sense block 1204. If the decision block 1208 makes an initial determination that capture did not occur, then the method 1200 continues in an auto sensitivity block 1212.

The auto sensitivity block 1212 aims to adjust sensitivity to enhance sensing of any native activity that may be present after the initial non-capture determination. After and/or during the enhanced sensing period, a decision block 1216 determines if any significant cardiac activity was sensed (e.g., activity above a noise, a sensing, a detection and/or a response threshold, etc.). If the decision block 1216 determines that no significant cardiac activity was sensed, then the method 1200 continues in a non-capture verification block 1220. However, if significant cardiac activity was sensed, then the method 1200 continues in a fusion and/or pseudofusion recognition block 1224.

In this exemplary method, a morphology discrimination block 1232 follows the recognition block 1224. Of course, other exemplary method may implement morphology discrimination at an earlier stage. According to previously discussed morphology discrimination features, a decision block 1232 compares one or more portions of sensed cardiac activity with one or more templates (e.g., characteristic of native activity). In this example, the decision block 1232 determines whether the sensed cardiac activity (which may be no activity) acquired using auto sensitivity has limited native activity. If the waveform has limited native activity, then the beat is classified as a fusion beat per a fusion block 1240; otherwise, the beat is classified as a pseudofusion beat per a pseudofusion block 1236.

Exemplary Recognition Algorithms for Advanced Therapy

As already mentioned, fusion and/or pseudofusion beats may seriously interfere with objectives of some algorithms and therapies. For example, an algorithm that detects capture (e.g., autocapture) may misinterpret a fusion waveform or a pseudofusion waveform as a loss of capture and, in response, deliver a back-up stimulus. Various exemplary recognition algorithms presented herein can improve performance of autocapture algorithms and therapies by recognizing fusion and/or pseudofusion beats. In addition, various recognition algorithms can improve hypertrophic obstructive cardiomyopathy therapies by recognizing fusion and/or pseudofusion beats. Again, in hypertrophic obstructive cardiomyopathy patients having adequate AV nodal conduction, if the AV interval is too long, the risk of fusion and pseudofusion increases and hence, so does the risk of inadequate ventricular action. Thus, exemplary recognition algorithms may recognize fusion and/or pseudofusion beats and adjust therapy accordingly.

Further, various exemplary recognition algorithms can improve multisite pacing therapies for dilated cardiomyopathy and congestive heart failure that rely on fusion. In particular, exemplary recognition algorithms that differentiate fusion from pseudofusion can be used to improve timing and hence increase the number of fusion beats.

CONCLUSION

Although exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and/or devices.

What is claimed is:
1. A method comprising:
 delivering a stimulus;
 sensing cardiac activity;
 determining whether the stimulus results in capture; and
 if the determining indicates that the stimulus did not result in capture, then determining whether the sensed cardiac activity includes characteristics of native cardiac activity by comparing at least some of the sensed cardiac activity to a cardiac activity template and distinguishing from the sensed cardiac activity an indicator of fusion or pseudofusion if the sensed cardiac activity includes native cardiac activity.

2. The method of claim 1, further comprising delivering a back-up stimulus if the stimulus did not result in capture and the sensed cardiac activity fails to include characteristics of native cardiac activity.

3. The method of claim 1, wherein the sensing occurs during an evoked response detection window.

4. The method of claim 1, wherein the sensing occurs after expiration of an evoked response detection window.

5. The method of claim 1, wherein an autocapture algorithm directs the delivering.

6. The method of claim 1, further comprising:
 responsive to determining that the sensed cardiac activity includes characteristics of native cardiac activity, inhibiting delivery of a back-up stimulus.

7. The method of claim 6, further comprising:
 responsive to determining that the sensed cardiac activity includes characteristics of native cardiac activity, adjusting a timing parameter for a subsequent stimulus.

8. A method comprising:
 delivering a ventricular stimulus;
 sensing ventricular cardiac activity;
 determining whether the ventricular stimulus resulted in ventricular capture; and
 if the determining indicates that the ventricular stimulus did not result in ventricular capture, then determining whether the sensed cardiac activity includes characteristics of native cardiac activity by comparing at least some of the sensed cardiac activity to a cardiac activity template and distinguishing from recognizing the sensed cardiac activity an indicator of fusion or pseudofusion if the sensed cardiac activity includes characteristics of native cardiac activity.

9. The method of claim 8, wherein the template comprises characteristics of native cardiac activity.

10. The method of claim 8, further comprising:
responsive to determining that the stimulus did not result in capture and the sensed cardiac activity failed to include characteristics of native cardiac activity, delivering a back-up stimulus and adjusting one or more parameters of subsequent stimuli.

11. The method of claim 8, further comprising:
responsive to determining that the stimulus did not result in capture and the sensed cardiac activity includes characteristics of native cardiac activity, inhibiting delivery of a back-up stimulus.

12. An implantable pacing device comprising:
means for determining whether a stimulus resulted in capture; and
if the means for determining indicates that the stimulus did not result in capture, then means for comparing sensed cardiac activity to a template to distinguish therefrom whether fusion or pseudofusion occurred.

13. The device of claim 12, wherein the stimulus is a ventricular stimulus and the sensed activity is ventricular cardiac activity.

14. The device of claim 12, further comprising means for providing a back-up stimulus if the stimulus did not result in capture.

15. The device of claim 12, further comprising means for adjusting one or more parameters of subsequent stimuli if fusion or pseudofusion occurred.

16. The device of claim 12, further comprising means for adjusting one or more parameters of subsequent stimuli if the stimulus did not result in capture.

17. The device of claim 12, further comprising means for inhibiting delivery of a back-up stimulus if the stimulus did not result in capture and fusion or pseudofusion occurred.

18. The device of claim 12, wherein the template comprises characteristics of native cardiac activity.

* * * * *